United States Patent
Goble et al.

[19]

[11] Patent Number: 6,036,694

[45] Date of Patent: Mar. 14, 2000

[54] SELF-TENSIONING SOFT TISSUE FIXATION DEVICE AND METHOD

[75] Inventors: E. Marlowe Goble, Logan; Thomas Wade Fallin; Daniel A. Perkins, both of Hyde Park, all of Utah

[73] Assignee: Innovasive Devices, Inc., Logan, Utah

[21] Appl. No.: 09/128,210

[22] Filed: Aug. 3, 1998

[51] Int. Cl.[7] .................................................. A61B 17/56
[52] U.S. Cl. ................................. 606/72; 606/73; 623/13
[58] Field of Search ................................ 606/60, 72, 73, 606/99, 104; 623/13

[56] References Cited

U.S. PATENT DOCUMENTS

| Re. 34,293 | 6/1993 | Goble et al. . |
|---|---|---|
| 4,301,551 | 11/1981 | Dore et al. . |
| 4,400,833 | 8/1983 | Kurland . |
| 4,467,478 | 8/1984 | Jurgutis . |
| 4,590,928 | 5/1986 | Hunt et al. . |
| 4,597,766 | 7/1986 | Hilal et al. . |
| 4,605,414 | 8/1986 | Czajka . |
| 4,668,233 | 5/1987 | Seedhom et al. . |
| 4,712,542 | 12/1987 | Daniel et al. . |
| 4,744,793 | 5/1988 | Parr et al. . |
| 4,772,286 | 9/1988 | Goble et al. . |
| 4,773,417 | 9/1988 | Moore et al. . |
| 4,834,752 | 5/1989 | Van Kampen . |
| 4,870,957 | 10/1989 | Goble et al. . |
| 4,927,421 | 5/1990 | Goble et al. . |
| 4,950,270 | 8/1990 | Bowman et al. . |
| 4,997,433 | 3/1991 | Goble et al. . |
| 5,037,426 | 8/1991 | Goble et al. . |
| 5,129,902 | 7/1992 | Goble et al. . |
| 5,139,520 | 8/1992 | Rosenberg . |
| 5,147,362 | 9/1992 | Goble . |
| 5,713,897 | 2/1998 | Goble et al. . |
| 5,766,250 | 6/1998 | Chervitz et al. .......................... 623/13 |

*Primary Examiner*—Michael Buiz
*Assistant Examiner*—Julian W. Woo
*Attorney, Agent, or Firm*—Allen, Dyer, Doppelt, Milbrath & Gilchrist, P.A. Attorneys at Law

[57] ABSTRACT

The device for affixing a flexible load-bearing element within a bone tunnel includes a securing element that attaches to the flexible element. A bone tunnel fixation element has an outer surface that is adapted to movably engage the bone tunnel. A deformable biasing element is positionable within the fixation element bore adjacent the proximal end. A locking member is dimensioned for movement within the fixation element bore and is positionable adjacent the distal end thereof. The locking member is lockable to the securing element, and the biasing means is for biasing the locking member toward the bore's distal end. Thus as a tension is applied to the securing means, a deformation of the biasing element is caused that is indicative of a magnitude of the applied tension. Therefore, a common element serves to perform pretensioning, and the need for a separate tensioning system is obviated.

32 Claims, 5 Drawing Sheets

SELF-TENSIONING SOFT TISSUE FIXATION DEVICE AND METHOD

BACKGROUND OF THE INVENTION

1. Field of the Invention

The present invention relates to surgical devices for use in fixating soft tissue to bone and, more particularly, to such devices for fixating soft tissue within a bone tunnel.

2. Description of Related Art

Orthopedic surgical procedures sometimes require an attachment (or reattachment) of a flexible member to a bone. The flexible member might comprise soft tissue such as a ligament or tendon, a synthetic element, or suture. Devices and methods are known in the art to accomplish such an attachment, including those for affixing the flexible member within a hole of the bone.

For example, it is known to use a member such as a screw to press at least one end of the flexible member against the interior wall of a bone space (Mahony, U.S. Pat. No. 5,062,843; Roger et al., U.S. Pat. No. 5,383,878; Steininger et al., U.S. Pat. No. 5,425,767; Huebner, U.S. Pat. No. 5,454,811; Laboureau, EU 0 317 406). It is also known to anchor a ligament between two elements, the inner one deformable (U.S. Pat. No. 5,108,431), and to pass a ligament through a center of a device, creating tension by relative movement of elements (DeSatnick, U.S. Pat. No. 5,571,184). It is further known to affix an implant to a bone surface (Hunt et al., U.S. Pat. No. 4,590,928).

In the general field of prosthetic ligaments, it is known to use a autograft or allograft to replace a length of connective tissue (Goble et al., U.S. Pat. Nos. 4,772,286; 4,870,957; 4,927,421; 4,997,433; 5,129,902; 5,147,362; U.S. Pat. No. Re. 34,293; Kurland, U.S. Pat. No. 4,400,833; Jurgutis, U.S. Pat. No. 4,467,478; Hilal et al., U.S. Pat. No. 4,597,766; Seedhom et al., U.S. Pat. No. 4,668,233; Parr et al., U.S. Pat. No. 4,744,793; Van Kampen, U.S. Pat. No. 4,834,752; Rosenberg, U.S. Pat. No. 5,139,520). Dore et al. teach the use of a tension spring for use as an artificial prosthetic ligament (U.S. Pat. No. 4,301,551).

Devices are also known for driving and affixing soft tissue to a desired site, typically a bone (Seedhom et al., U.S. Pat. No. 4,668,233; Daniel et al., U.S. Pat. No. 4,712,542; Goble et al., '902; Rosenberg, U.S. Pat. No. 5,139,520).

An additional problem includes the establishment and maintenance of a desired tension in a graft in order to provide optimal postoperative mobility and support. This has been addressed by Daniel et al. ('542) and by Goble et al. (U.S. Pat. Nos. 5,037,426; 5,713,897).

A particular surgery in which flexible member attachment is required is the reattachment of soft tissue, such as is required in the affixing of a ligament to a bone. A particular procedure is the reattachment of an anterior cruciate ligament or the attachment of a graft within a bone tunnel.

However, there is no known effective device and method for pretensioning the soft tissue/graft to a known preload without the use of a separate tensioning system, which is advantageous in restoring optimal physiological operation. Nor is there known to be such a device and method for attaching a soft tissue/graft within a bone tunnel wherein the a substantial portion of the load is borne by the bone exterior.

SUMMARY OF THE INVENTION

It is therefore an object of the present invention to provide a device and method for affixing a flexible member to a bone.

It is an additional object to provide such a device and method for affixing a flexible member to a bone under a predetermined tension.

It is a further object to provide such a device and method that performs the dual functions of implanting and pretensioning.

It is another object to provide such a device and method that permits a substantial portion of the load to be borne by an external, stronger portion of the bone.

It is also an object to provide a device and method for inserting a fixation device.

These objects and others are attained by the present invention, a device for affixing a flexible load-bearing element within a bone tunnel. The device comprises a securing means that has a proximal portion, which in turn has means for attaching to the flexible element. The securing means further has a distal portion having engagement means.

The device further comprises bone tunnel fixation means, which has a bore therethrough from a distal end to a proximal end. The fixation means further has an outer surface that is adapted to movably engage a bone tunnel. In a particular embodiment, such an outer surface may comprise a threaded surface for screwing into a bone tunnel, although this is not intended as a limitation.

Deformable biasing means are included that is positionable within the fixation means bore adjacent the proximal end. A locking member is dimensioned for movement within the fixation means bore and is positionable adjacent the distal end thereof. The locking member has means for locking the engagement means thereto, and the biasing means is for biasing the locking member toward the bore's distal end. Thus as a tension is applied to the securing means, a deformation of the biasing means is caused, which is indicative of a magnitude of the applied tension. Therefore, a common element serves to perform pretensioning, and the need for a separate tensioning system is obviated. Such a device assists in maintaining and/or restoring optimal physiological operation.

A second embodiment of the device for affixing a flexible load-bearing element within a bone tunnel comprises sleeve means. The sleeve means has a proximal portion that is adapted to reside within a bone tunnel, the proximal portion having a passage that extends from the proximal end. The sleeve's distal portion has means for resisting movement into the bone tunnel.

The device also comprises sleeve fixation means, which has a bore therethrough and an outer surface that is adapted to movably engage the sleeve means passage.

The remaining elements of the device, the securing means, biasing means, and locking member are as above for the first embodiment.

The second embodiment of the device has particular utility in cases in which the internal bone may have insufficient strength to support the load imposed upon the device. It can be seen that a great portion of the load is instead borne by the external surface of the bone, which is stronger than the porous interior.

A method of the present invention is for affixing a flexible load-bearing element within a bone tunnel. The first embodiment of the method comprises the steps of gripping a distal end of a flexible member, which may include soft tissue or a soft tissue graft. Next the flexible member's distal end is inserted into a bone tunnel and is retained within a fixation member movably affixed within the bone tunnel.

The flexible member end is biased in a proximal direction by means of spring means housed within the fixation member. A load upon the flexible member can be determined from a deformation of the spring means. The tension upon the flexible member can be adjusted by moving the fixation member in the appropriate direction to either increase or decrease the load to a desired value.

A second embodiment of the method comprises the steps of positioning a sleeve within a bone tunnel, the sleeve having a passage therethrough and means for resisting a movement into the bone tunnel at a distal end. Next a distal end of a flexible member is gripped. The flexible member distal end is inserted into a bone tunnel, and the flexible member distal end is retained within a fixation member that is movably affixed within the sleeve.

As above, the flexible member end is biased in a proximal direction with spring means housed within the fixation member, a load upon the flexible member is determined from a deformation of the spring means.

A system for affixing a flexible load-bearing element and further for determining a load thereupon includes the devices as described above and an indicating driver comprising an elongated driving portion that has a bore therethrough and means at a first end for drivably engaging the fixation means. The driver further comprises plunger means that is positioned for movement within the driving portion bore. The plunger means has a first end that is biased for protrusion from the driving portion's first end and is adapted for contacting the locking member. The driver also comprises indicator means positioned in spaced relation from the first end, so as to be visualizable by the user, for measuring the distance between the driving portion's first end and the plunger means's first end. This distance is indicative of the deformation of the biasing means, and can then be used to determine if the desired load has been placed upon the flexible load-bearing member.

In addition, the indicating driver can be used to change the position within the tunnel of the fixation means, thereby changing the load to a predetermined desired value.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be presented with reference to FIGS. 1–7.

The Fixation Device

A preferred embodiment of the fixation device 10 of the present invention comprises four elements acting cooperatively to affix an end of an flexible load-bearing element 11 within a bone tunnel 13.

Figure 1:
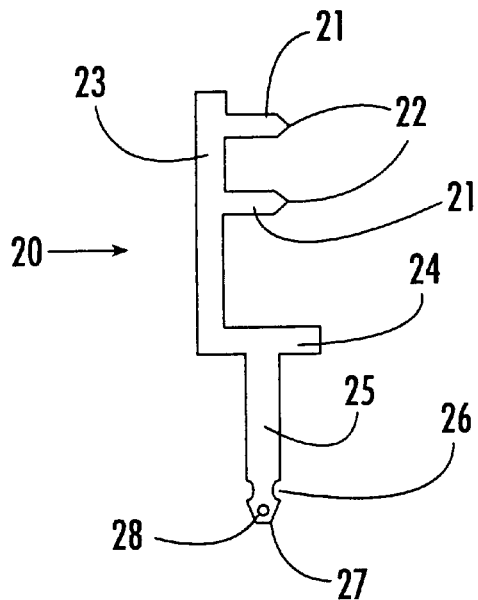
FIG. 1 is a perspective side view of the soft tissue securing element.
Figure 2:
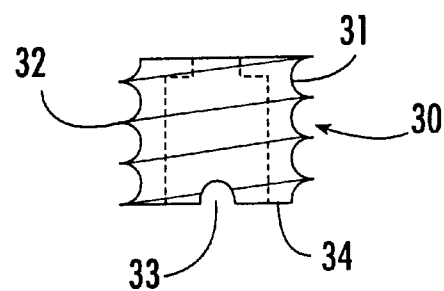
FIG. 2 is a perspective side view of the bone fixation element.
Figure 3:
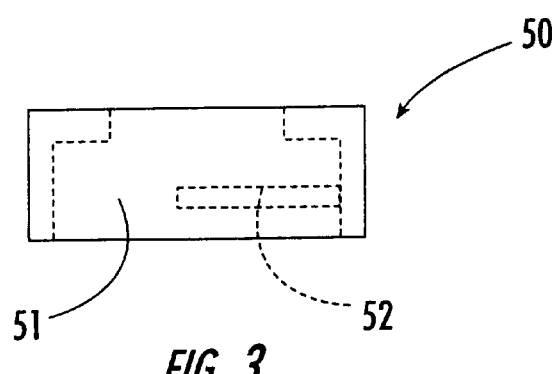
FIG. 3 is a perspective side view of the locking member.

A securing element 20 has a proximal portion that has means for attaching to a distal end of the flexible element 11. As illustrated in FIG. 1, the attaching means comprises at least one barb, here two barbs 21, each having a pointed end 22 that is sufficiently sharp to impale a flexible element thereon. The barbs 21 protrude inwardly from an arm 23 that extends generally normal from an outer edge of a central disk 24 that is oriented generally normal to a longitudinal axis of the securing element 20.

The securing element 20 further has a distal portion that comprises a post 25 extending from the center of the disk 24. The post 25 has an outer circumferential groove 26 adjacent the distal end 27. The post 25 has means at the distal end for engaging a pulling element for drawing the distal portion into the bone tunnel fixation means bore 31 from a distal end of the bone tunnel. In a particular embodiment the pulling element engaging means comprises a portal 28 through the distal portion adjacent the distal end, the portal 28 being dimensioned for passing a flexible puller therethrough. Such a flexible puller may comprise, for example, a length of suture material or a wire, although these are not intended as limitations.

The device 10 additionally comprises a generally cylindrical fixation element 30 (FIG. 2), which has a bore 31 therethrough extending from the proximal end to the distal end 34. At the proximal end the bore 31, which has a first diameter from the distal end through a central portion, narrows to a second diameter smaller than the first diameter. The outer surface includes a helical ridge 32 thereon for screwingly engaging a bone tunnel and for permitting movement therewithin.

The bone tunnel fixation element 30 further has means at the distal end 34 for being driven by a driver. In a particular embodiment such means comprises at least one slot, here four slots 33, in the distal surface projecting inwardly from the outer surface and not communicating with the bore 31. The slots 33 are for mating with a driver protrusion, which is adapted to turn the bone tunnel fixation means.

The device 10 further comprises a deformable biasing element that is positionable within the wider portion of the fixation element's bore 31. Such a biasing element may comprise, for example, a spring 40, such as a belleville, wavy, or curved spring, although these are not intended as a limitation (see FIG. 7). The spring 40 has a bore 41 therethrough positioned for alignment with the narrowed portion of the fixation element's bore 31 and dimensioned to permit the securing element's post 25 to pass therethrough.

Finally, the device 10 includes a generally cylindrical locking member 50 (FIG. 3) that has an opening dimensioned to admit at least a distal section of the post 25. In the preferred embodiment the opening comprises a bore 51 from the distal end to the proximal end, the bore 51 narrowed at the proximal end. Positioned within the bore 51 is a deformable member, such as a wire 52, extending into the bore 51 in an off-center orientation. The wire 52 is movable between a first position, wherein it resides within the post groove 26, and a second position, wherein the post's distal section is permitted to pass thereby. Force is required to deform the wire 52 to the second position, since it is biased to the first position, so that, when the wire 52 has snapped into the groove 26, it will remain there unless force is exerted to extract it therefrom.

Figure 4:
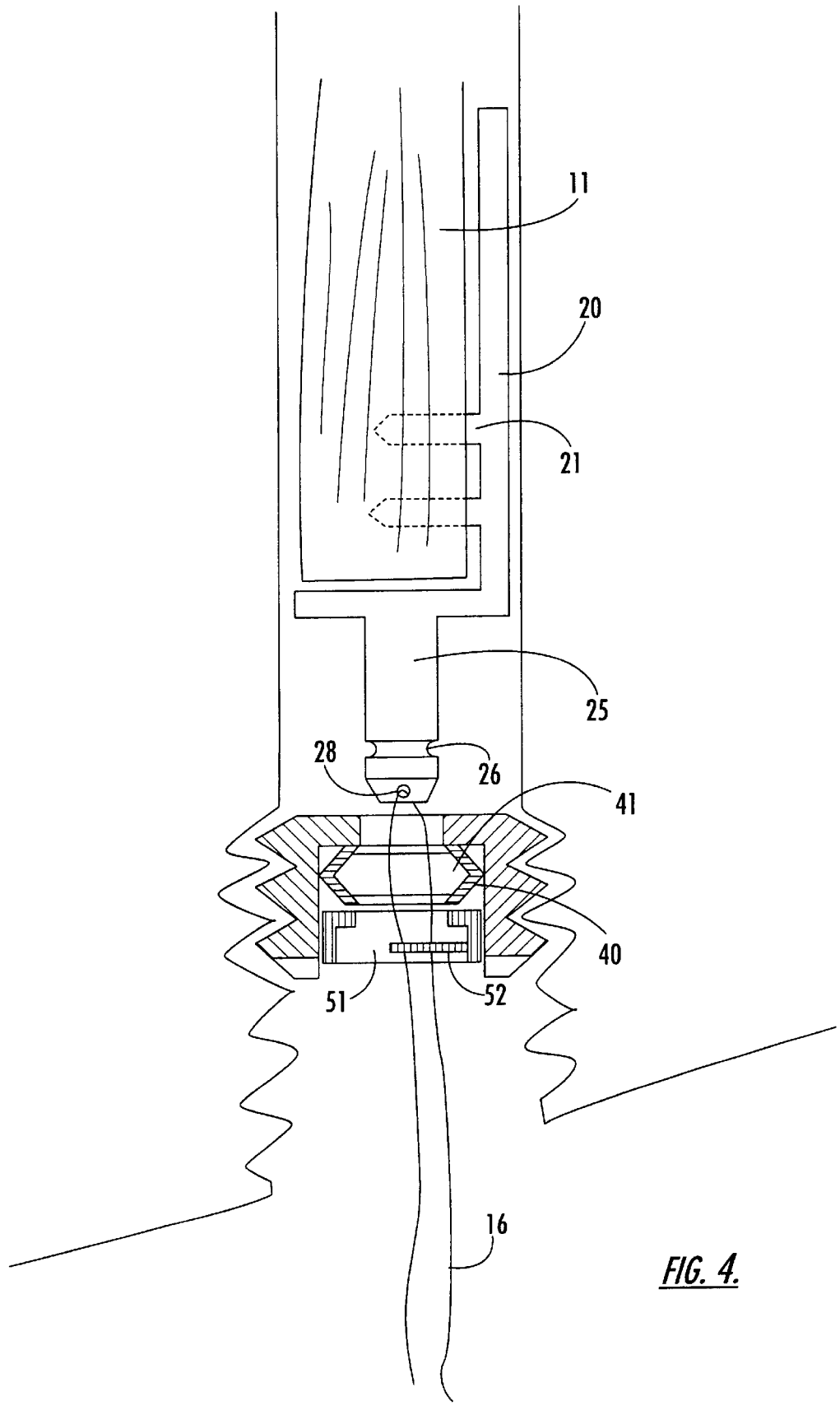
FIG. 4 is an axial cross-sectional view of the fixation device in position within a bone tunnel, prior to locking.
Figure 5:
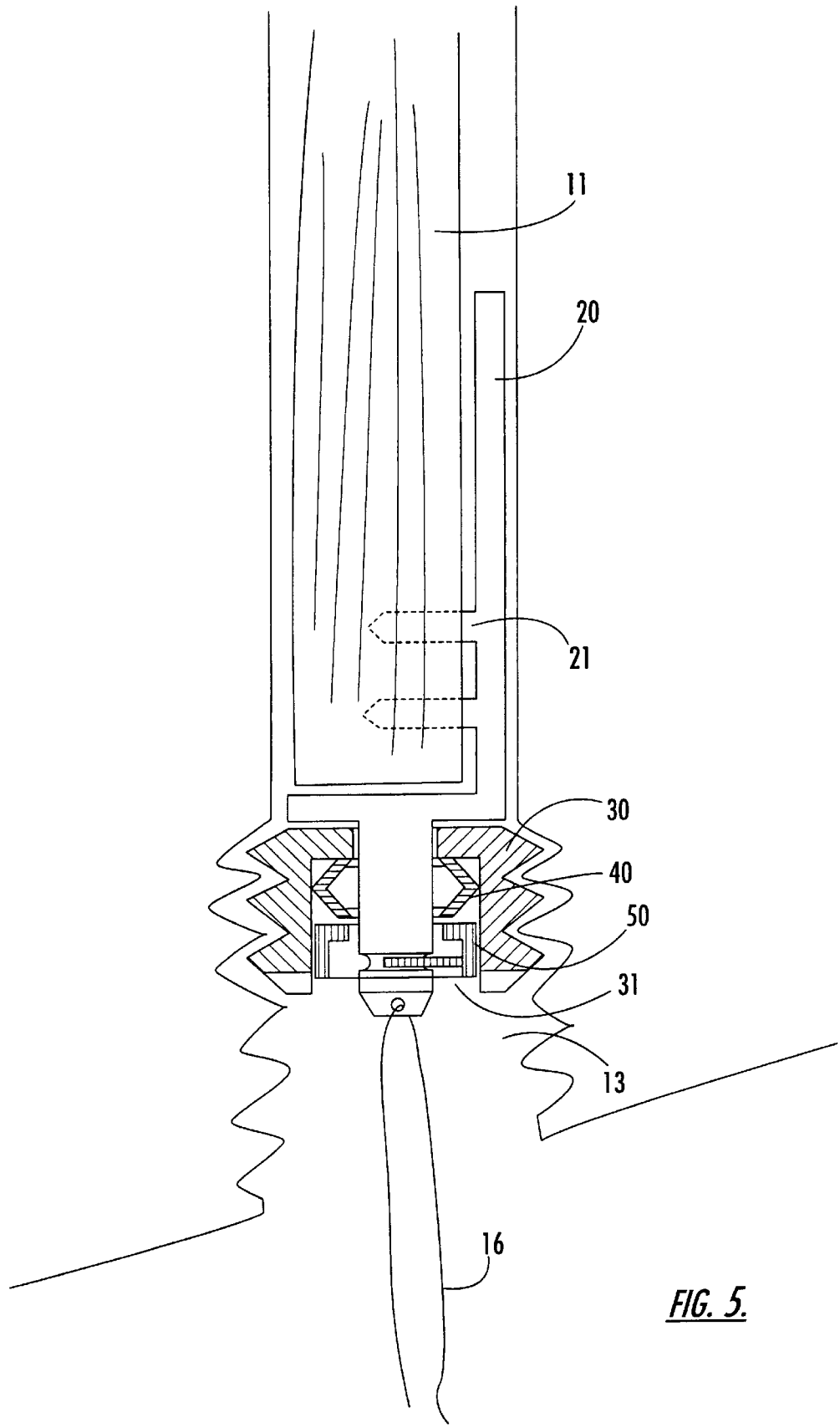
FIG. 5 is an axial cross-sectional view of the fixation device in position within a bone tunnel, after locking.
Figure 6:
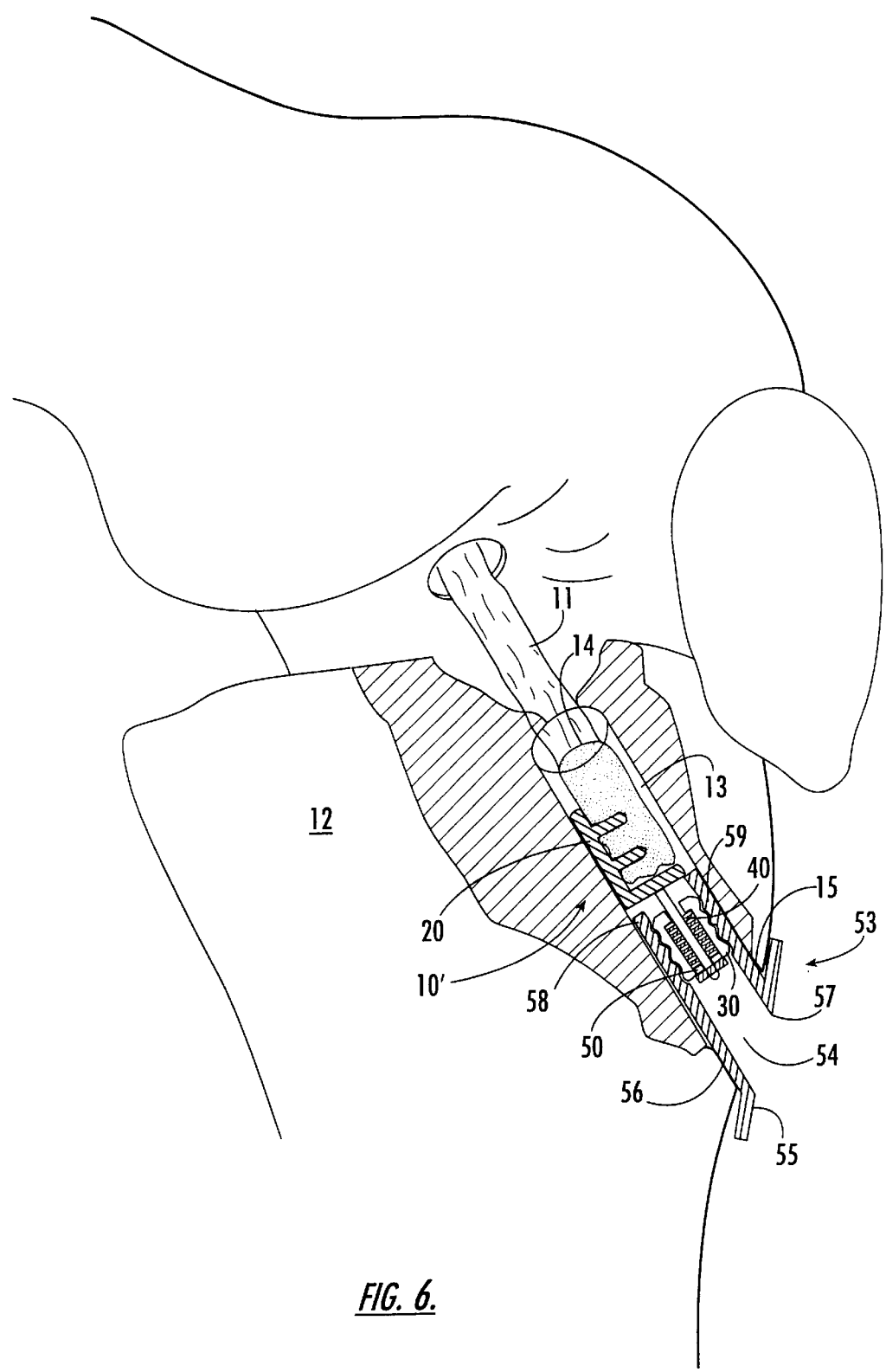
FIG. 6 is an axial cross-sectional view of the second embodiment of the fixation device in position within a bone tunnel, after locking.

In use, the device 10 is utilized as illustrated in FIGS. 4 and 5. The barbs 21 of the securing element 20 are inserted into the distal end of the flexible member 11 (e.g., tendon, ligament, prosthetic). The fixation element 30, with the spring 40 and locking member 50 in place within its bore 31, is screwed into the bone tunnel 13 from the tunnel's distal end.

A flexible material, such as suture 16, is inserted through the portal 28 in the post 25 of the securing element 20. The suture 16 is drawn through the bores 31,41,51 of the fixation element 30, spring 40, and locking member 50 to emerge from the distal end of the bone tunnel 13. The suture 16 is pulled to draw the post 25 into the bores 31,41,51 until the wire 52 locks the post 25 in place, which in turn locks the flexible member 11 in place. It can be seen that any movement of the fixation element 30 in a distal or proximal direction will, respectively, increase or decrease the load on the flexible member 11, and that a deformation of the spring 40 is indicative of this load.

A second embodiment of the device 10' comprises, in a preferred embodiment, the elements essentially as described above. An additional element comprises a sleeve 53, which has a proximal portion 56 that is adapted to reside within the bone tunnel 13. The proximal portion 56 has a passage 54 that extends from a proximal end 58 and a distal portion that has means for resisting movement into the bone tunnel 13. In a first subembodiment, the movement-resisting means comprises a flange 55 that surrounds the distal end of the passage 54. The flange 55 is adapted to abut the distal end 15 of the bone tunnel 13.

In a second subembodiment, the movement-resisting means comprises at least one tab (not shown) affixed adjacent and extending outwardly therefrom at an angle to the distal end of the passage 54.

In these subembodiments the fixation element 30 comprises a sleeve fixation means, and sleeve's passage 54 has a threaded proximal section 59 that is adapted for screwingly engaging the helical ridge 32.

The method for affixing a flexible load-bearing element within a bone tunnel using the second embodiment of the device 10' comprises the steps of positioning the sleeve 53 within the bone tunnel 13, and gripping the distal end of the flexible member 11, which is then inserted into the bone tunnel 13.

The flexible member's distal end is retained within a fixation element 30, which is screwed into the threaded section 59 of the sleeve 53. As before, the flexible member end is biased in a proximal direction with a spring 40 housed within the fixation element bore 31. Also, again, a load upon the flexible member 11 is determined from a deformation of the spring 40.

The load upon the flexible member 11 can be adjusted to a desired value by moving the fixation element 30 within the sleeve 53 in a direction appropriate for effecting the desired load adjustment.

The Indicating Driver

Figure 7:
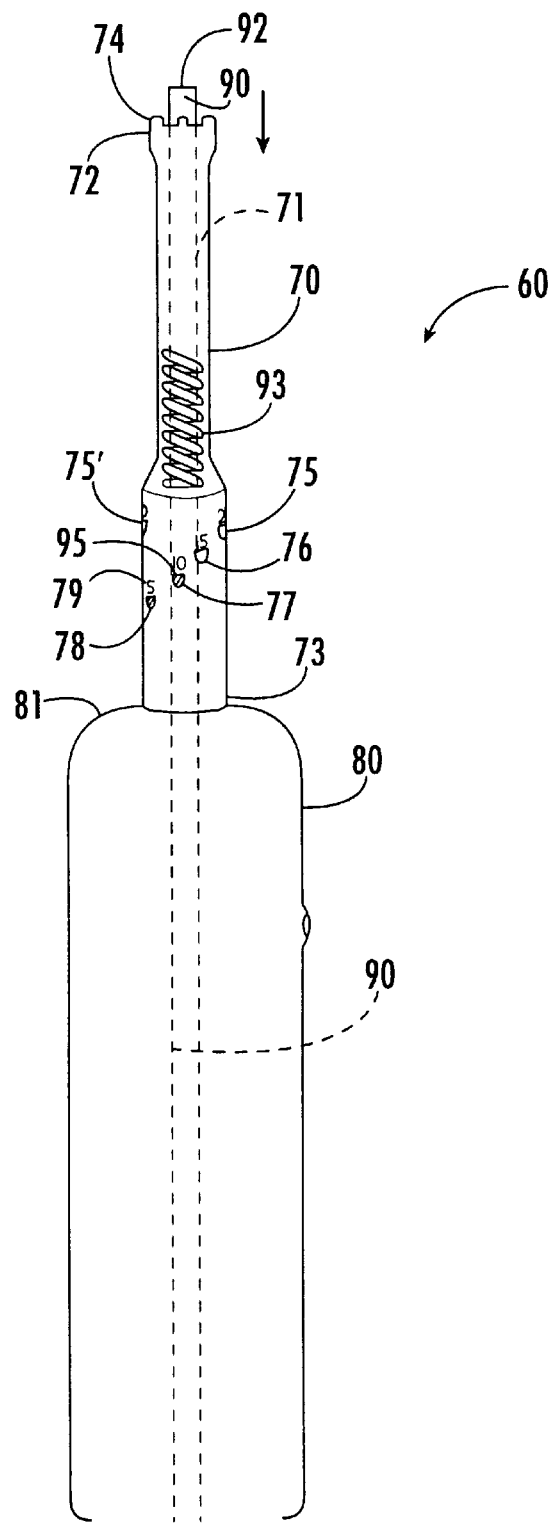
FIG. 7 is an axial view of the indicating driver.

Another aspect of the present invention comprises an indicating driver 60 for inserting and adjusting the position of the fixation element 30 and also for indicating the spring's 40 deformation and, hence, load (FIG. 7).

The driver 60 comprises an elongated generally cylindrical driving portion 70 that has a bore 71 therethrough extending from a first end 72 to a second end 73. The driving portion's second end 73 is affixed to a driver body, a handle 80, adjacent a first end 81 thereof. Means, such as four protrusions 74, are positioned at the driving portion's first end 72 for drivably engaging the fixation element's slots 33.

The driving portion 70 has a plurality of windows, here, eight windows 75–78,75'–78', extending from the outer surface through to the bore 71, and positioned in spaced relation from the first end 72. In a particular embodiment, the windows are pairwise staggered along the longitudinal extent of the driving portion 70, with each pair, e.g., 75,75' 180 degrees from each other around the circumference of the driving portion 70, and the next pair, 76,76', closer to the first end 72 and separated from the first pair 75,75' by 45 degrees, etc. Indicia 79 are located adjacent each window, the purpose of which will be described in the following.

Slidably positioned within the driving portion's bore 71 is an elongated, generally cylindrical plunger 90, which has a portion extending out of the bore 71 beyond the driving portion's first end 72. The plunger 90 is biased so that the plunger's first end 92 is biased for extension away from the body 80 and for protrusion from the driving portion's first end 72. This biasing is accomplished with a spring 93 positioned between respective shoulders of the plunger 90 and driving portion 70 by means well known in the art.

The plunger's first end 92 is adapted for contacting the locking member 50; in particular, the plunger's first end 92 is dimensioned for insertion within the fixation element's bore 31 sufficiently far to contact the locking member 50. The driving portion's first end 72, however, is too large to enter the fixation element's bore 31; therefore, the distance between the locking member 50 and the fixation element's distal end 34 is reflected by the distance between the plunger's first end 92 and the driving portion's first end 72.

The indicating driver 60 additionally comprises an indicator element, here a marking 95 on the outside of the plunger 90, such as, but not limited to, a colored band. The marking 95 is positioned for successive visualization through the windows 75–78,75'–78', so that, as the plunger 90 moves within the driving portion's bore 71, the position of the marking 95 indicates via the indicia 79 the applied tension.

In use, then, as the plunger 90 is biased toward the locking member 50 when in position within the bone tunnel 13, locating the is driving portion's protrusions 74 within the slots 33 of the fixation element 30 permits the plunger 90 to proceed into the fixation element's bore 31. The plunger 90 extends in a proximal direction as far as possible until it impinges upon the locking member 50. The user is then able to read a value from the indicia 79 on the driving portion 70.

If desired, while in this position, the driver 60 is turned in a direction appropriate to effect a change in the load until the load indicated is that desired by the user.

A particular use for this system, although this is not intended as a limitation, is in the attachment of a tendon 11 within a tunnel 13 in a tibia 12 to reconstruct a knee joint.

It may be appreciated by one skilled in the art that additional embodiments may be contemplated, including other indicating mechanisms for measuring load and alternate locking mechanisms for affixing a flexible member within a bone tunnel.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A device for affixing a flexible load-bearing element within a bone tunnel, the device comprising:
   securing means having a proximal portion having means for attaching to the flexible element and a distal portion having engagement means;
   bone tunnel fixation means having a bore therethrough and an outer surface adapted to movably engage a bone tunnel;
   deformable biasing means positionable within the fixation means bore adjacent a proximal end thereof; and
   a locking member dimensioned for movement within the fixation means bore and positionable adjacent a distal end thereof, having means for locking the engagement means thereto, the biasing means for biasing the locking member toward the bore distal end, and the securing means for causing a deformation of the biasing means indicative of a magnitude of an applied tension.

2. The device recited in claim 1, wherein the securing means attaching means comprises at least one barb having a pointed end sufficiently sharp to impale a flexible element thereon.

3. The device recited in claim 1, wherein the securing means further has:
   a central disk generally normal to a longitudinal axis; and
   a proximal portion comprising an arm extending generally normal from an outer edge of the disk and a plurality of barbs extending inwardly from the arm.

4. The device recited in claim 3, wherein:
   the securing means distal portion comprises a post extending from the disk, the post having an outer circumferential groove therein adjacent a distal end; and
   the locking member has an opening dimensioned to admit at least a distal section of the securing means distal portion and a deformable member positioned within the opening, the member movable between a first position adapted to reside within the post groove and a second position adapted to permit the post distal section to pass thereby, the member biased to the first position.

5. The device recited in claim 1, wherein the bone tunnel fixation means comprises a generally cylindrical member having an outer surface having a helical ridge thereon for screwingly engaging a bone tunnel.

6. The device recited in claim 5, wherein the bone tunnel fixation means further has means at a distal end for being driven by a driver.

7. The device recited in claim 6, wherein the means for being driven comprises at least one slot for mating with a driver protrusion adapted to turn the bone tunnel fixation means.

8. The device recited in claim 6, wherein the bone tunnel fixation means bore has a first diameter at a distal end and a second diameter at a proximal end, the first diameter sufficiently large to admit the biasing means thereinto, the second diameter sufficiently small to prevent the biasing means from passing thereinto.

9. The device recited in claim 1, wherein the biasing means comprises a spring adapted to permit the securing means distal portion to pass therepast.

10. The device recited in claim 1, wherein the locking member has a bore generally coaxial with the fixation means bore and the securing means distal portion comprises a post dimensioned for insertion into the locking member bore.

11. The device recited in claim 10, wherein the post has an outer circumferential groove adjacent a distal end and the locking member has a deformable wire extending into the locking member bore in a generally off-center orientation, the wire movable between a first position residing within the post groove and a second position wherein the post distal section is permitted to pass thereby, the wire biased to the first position.

12. The device recited in claim 1, wherein the securing means distal portion comprises a post having means at a distal end for engaging a pulling element for drawing the distal portion into the bone tunnel fixation means bore from a distal end of the bone tunnel.

13. The device recited in claim 12, wherein the pulling element engaging means comprises a portal through the distal portion dimensioned for passing a flexible puller therethrough.

14. A method for affixing a flexible load-bearing element within a bone tunnel, the method comprising the steps of:
   gripping a distal end of a flexible member;
   inserting the flexible member distal end into a bone tunnel;
   retaining the flexible member distal end within a fixation member movably affixed within the bone tunnel;
   biasing the flexible member end in a proximal direction with spring means housed within the fixation member; and
   determining a load upon the flexible member from a deformation of the spring means.

15. The method recited in claim 14, further comprising the step of adjusting the load upon the flexible member to a desired value by moving the fixation member within the bone tunnel in a direction appropriate for effecting the desired load adjustment.

16. A device for affixing a flexible load-bearing element within a bone tunnel, the device comprising:
   sleeve means having a proximal portion adapted to reside within a bone tunnel having a passage extending from a proximal end and a distal portion having means for resisting movement into the bone tunnel;
   securing means having a proximal portion having means for attaching to the flexible element and a distal portion having engagement means;
   sleeve fixation means having a bore therethrough and an outer surface adapted to movably engage the sleeve means passage;
   deformable biasing means positionable within the fixation means bore adjacent a proximal end thereof; and
   a locking member dimensioned for movement within the sleeve fixation means bore and positionable adjacent a distal end thereof, having means for locking the engagement means thereto, the biasing means for biasing the locking member toward the bore distal end, and the securing means for causing a deformation of a biasing means indicative of a magnitude of the applied tension.

17. The device recited in claim 16, wherein the sleeve means passage has a threaded proximal portion and the sleeve fixation means comprises a generally cylindrical member having an outer surface having a helical ridge thereon for screwingly engaging the sleeve means passage threaded proximal portion.

18. The device recited in claim 16, wherein the sleeve means passage extends from the proximal end through to a distal end, and wherein the movement-resisting means comprises flange means in surrounding relation to the passage adapted to abut a distal end of the bone tunnel.

19. The device recited in claim 16, wherein the sleeve means passage extends from the proximal end through to a distal end, and wherein the movement-resisting means comprises a tab extending outwardly from the sleeve away from the passage and adapted to abut a distal end of the bone tunnel.

20. A method for affixing a flexible load-bearing element within a bone tunnel, the method comprising the steps of:

positioning a sleeve within a bone tunnel, the sleeve having a passage therethrough and means for resisting a movement into the bone tunnel at a distal end;

gripping a distal end of a flexible member;

inserting the flexible member distal end into a bone tunnel;

retaining the flexible member distal end within a fixation member movably affixed within the sleeve;

biasing the flexible member end in a proximal direction with spring means housed within the fixation member; and determining a load upon the flexible member from a deformation of the spring means.

21. The method recited in claim 20, further comprising the step of adjusting the load upon the flexible member to a desired value by moving the fixation member within the sleeve in a direction appropriate for effecting the desired load adjustment.

22. A system for affixing a flexible load-bearing element within a bone tunnel and for determining a load upon the load-bearing element, the system comprising:

an affixing device comprising:
securing means having a proximal portion having means for attaching to the flexible element and a distal portion having engagement means;
bone tunnel fixation means having a bore therethrough and an outer surface adapted to movably engage a bone tunnel;
deformable biasing means positionable within the fixation means bore adjacent a proximal end thereof; and
a locking member dimensioned for movement within the fixation means bore and positionable adjacent a distal end thereof, having means for locking the engagement means thereto, the biasing means for biasing the locking member toward the bore distal end, and the securing means causing a deformation of the biasing means indicative of a magnitude of an applied tension; and an indicating driver comprising:
an elongated driving portion having a bore therethrough and means at a first end for drivably engaging the fixation means;
plunger means positioned for movement within the driving portion bore having a first end biased for protrusion from the driving portion first end and adapted for contacting the locking member; and
indicator means positioned in spaced relation from the first end having means for indicating a distance between the driving portion first end and the plunger means first end, the distance indicative of a deformation of the biasing means.

23. The system recited in claim 22, further comprising a handle affixed to a second end of the driving portion.

24. The system recited in claim 22, wherein the fixation means further has at least one slot at a distal end, and the driving portion engaging means comprises at least one protrusion dimensioned for insertion into the fixation means slot.

25. The system recited in claim 24, wherein the fixation means outer surface has a helical ridge thereon for screwingly engaging a bone tunnel.

26. The system recited in claim 22, wherein the driver further comprises spring means positioned in biasing relation between the plunger and the driving portion.

27. The system recited in claim 22, wherein the driving portion has a window extending from an outer surface through to the bore, and wherein the indicator means comprises a marking on the plunger positioned for visualization through the window.

28. The system recited in claim 22, wherein the driving portion has a plurality of windows positioned in staggered relation to each other and extending from an outer surface through to the bore, and wherein the indicator means comprises a marking on the plunger positioned for successive visualization through the windows as the plunger is moved within the driving portion bore.

29. The system recited in claim 28, wherein the driving portion has an indicium adjacent each window commensurate with an applied tension effected when the marking is visualizable therethrough.

30. A system for affixing a flexible load-bearing element within a bone tunnel and for determining a load upon the load-bearing element, the system comprising:

an affixing device comprising:
sleeve means having a proximal portion adapted to reside within a bone tunnel having a passage extending from a proximal end and a distal portion having means for resisting movement into the bone tunnel;
securing means having a proximal portion having means for attaching to the flexible element and a distal portion having engagement means;
sleeve fixation means having a bore therethrough and an outer surface adapted to movably engage the sleeve means passage;
deformable biasing means positionable within the fixation means bore adjacent a proximal end thereof; and
a locking member dimensioned for movement within the sleeve fixation means bore and positionable adjacent a distal end thereof, having means for locking the engagement means thereto, the biasing means for biasing the locking member toward the bore distal end, and the securing means for causing a deformation of the biasing means indicative of a magnitude of an applied tension; and an indicating driver comprising:
an elongated driving portion having a bore therethrough and means at a first end for drivably engaging the fixation means;
plunger means positioned for movement within the driving portion bore having a first end biased for protrusion from the driving portion first end and adapted for contacting the locking member; and
indicator means positioned in spaced relation from the first end having means for indicating a distance between the driving portion first end and the plunger means first end, the distance indicative of a deformation of the biasing means.

31. The system recited in claim 30, wherein the fixation means further has at least one slot at a distal end, and the driving portion engaging means comprises at least one protrusion dimensioned for insertion into the fixation means slot.

32. The system recited in claim 31, wherein the sleeve means passage has a threaded proximal portion and the sleeve fixation means comprises a generally cylindrical member having an outer surface having a helical ridge thereon for screwingly engaging the sleeve means passage threaded proximal portion.

* * * * *